United States Patent [19]
Russell et al.

[11] Patent Number: 6,096,734
[45] Date of Patent: Aug. 1, 2000

[54] PHOTOSENSITIZERS FOR SENSITIZING CELLS

[75] Inventors: David A Russell; Michael J Cook, both of Norwich, United Kingdom

[73] Assignee: The Secretary of State for Defence in Her Britannic Majesty's Government of the United Kingdom of Great Britain and Northern Ireland of Defence and Evaluation Research Agency, Hants, United Kingdom

[21] Appl. No.: 09/139,604

[22] Filed: Aug. 24, 1998

Related U.S. Application Data

[62] Division of application No. 08/596,287, Feb. 13, 1996, Pat. No. 5,834,455.

[30] Foreign Application Priority Data

Aug. 27, 1993 [GB] United Kingdom ............... 9317881
Aug. 24, 1994 [WO] WIPO ............... PCT/GB94/01847

[51] Int. Cl.$^7$ .................. A61K 31/555; A61K 31/40
[52] U.S. Cl. ............................... 514/185; 514/410
[58] Field of Search ................... 514/185, 410

[56] References Cited

U.S. PATENT DOCUMENTS 5,506,708  4/1996  Harrison ................. 359/103

FOREIGN PATENT DOCUMENTS 2229190  9/1990  United Kingdom .

*Primary Examiner*—Jerome P. Goldberg
*Attorney, Agent, or Firm*—Nixon & Vanderhye

[57] ABSTRACT

Susceptible tumors are treated by first sensitizing them to incident electromagnetic radiation by of a compound of the formula:

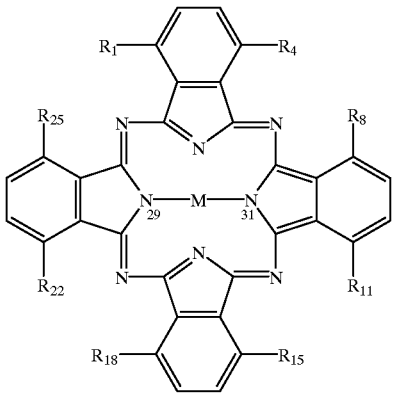

formula I where M is a diamagnetic metal ion or a diamagnetic metal compound or silicon or a compound of silicon or is 2H; one H being bonded to each of the two nitrogen atoms depicted as being bonded to M at positions 29 and 31;

$R_1$ to $R_{25}$ are the same or different and are independently selected from $C_1$–$C_{20}$, alkyl, $C_2$–$C_{20}$ alkenyl, X—O—Y,

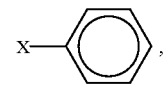

$X^2COOX^1$, $x^2COONR^1R^{11}$ and H;

wherein X and $X_2$ are independently selected from a chemical bond, —$(CH_2)_n$— where n is an integer from 1 to 20 and —$(CH_2)_a$CH=CH$(CH_2)_b$ where a and b are independently selected from integers 0–20 and a+b totals from 0 to 20;

$X^1$ is independently selected from $C_{1\text{-}20}$ alkyl, $C_{2\text{-}20}$ alkenyl and H;

$R^1$ and $R^{11}$ are independently selected from H, $C_{1\text{-}20}$ alkyl, $C_{2\text{-}20}$ alkenyl; and Y is independently selected from $C_{1\text{-}20}$ alkyl, $C_{2\text{-}20}$ alkenyl and H;

provided that not all $R_1$–$R_{25}$ are simultaneously H; and provided that not all $R_1$–$R_{25}$ are simultaneously n-alkoxy Thereafter tumors so treated are exposed to incident electromagnetic radiation which is absorbed by the compound (I).

20 Claims, 2 Drawing Sheets

PHOTOSENSITIZERS FOR SENSITIZING CELLS

This is a division of application Ser. No. 08/596,287, filed Feb. 13, 1996, now U.S. Pat. No. 5,834,455.

This invention relates to photosensitizers, more particularly it relates to their use in photodynamic therapy.

In the photodynamic therapy of cancer, dye compounds are administered to a tumour-bearing subject. These dye substances may be taken up, to a certain extent, by the tumour. Upon selective irradiation with an appropriate light source the tumour tissue is destroyed via the dye mediated photo-generation of species such as singlet oxygen or other cytotoxic species such as free radicals, for example hydroxy or superoxide.

A number of phthalocyanine (Pc) derivatives have been proposed as potential photodynamic therapeutic (PDT) agents. Most biological studies on Pc compounds related to PDT have been conducted with water soluble sulfonated metallo-phthalocyanines as described by I. Rosenthal, *Photochem. Photobiol.* 53(6), 859–870, 1991. Methods for synthesizing these compounds often results in mixtures of compounds containing a variety of isomers and/or different degrees of sulfonation. Drug regulatory agencies are becoming increasingly stringent in their requirements for substantially pure compounds, hence not being able to produce substantially pure compounds is a particular disadvantage with respect to pharmaceutical applications.

The combination of a sensitizer and electromagnetic radiation for the treatment of cancer is commonly known as photodynamic therapy.

Phthalocyanine has the following formula:

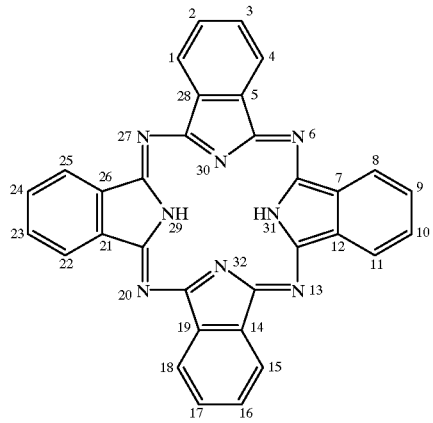

The nomenclature for the numbering of the phenyl ring is also included in the above depiction.

Metallated Pc's have been found to have better photosensitizing activity compared to metal-free phthalocyanines when the metal is diamagnetic. Conversely a paramagnetic metal renders the phthalocyanine inactive, see I. Rosenthal and E. Ben-Hur, *Phthalocyanines in photobiology* in *Phthalocyanines, Properties and Applications,* Ed., C. C. Leznoff and A. B. P. Lever, V. C. H. Publishers 1989. Photosensitization is a process in which a photochemical reaction is induced to occur by the presence of a substance (the photosensitizer) which absorbs the light but itself is substantially unchanged at the end of the reaction, the absorbed light energy being passed on to the main reactants. For example when hydrogen is exposed to light of wavelength 253.6 nm no absorption of the light takes place and the hydrogen remains completely unaffected. If mercury vapour is added to the hydrogen, the mercury atoms are excited. When such an excited mercury atom collides with a hydrogen molecule, it can transfer some of its energy to the hydrogen, and cause it to dissociate into atoms. The hydrogen has apparently been made sensitive to the light which it does not absorb. In some cases the photosensitizer is broken down and a photoproduct is formed which may also possess suitable PDT properties.

Similarly, oxygen can be made sensitive to the electromagnetic radiation it may not normally absorb by the presence of phthalocyanines or other 'complex' organic molecules; some of which may have metals or metal salts incorporated.

Patent WO 93/09124 describes the use of water soluble salt or acid forms of transition metal phthalocyanines for use in photodynamic therapy. In this patent application phthalocyanines containing second or third row transition metals with a $d^6$ low-spin electronic configuration are disclosed. The compounds exemplified in patent application WO 93/09124 contain Ru.

European Patent Application 0 484 027 A1 describes the use of substituted phthalocyanines for the generation of singlet oxygen.

UK Patent GB 2,229,190 B relates to certain novel substituted phthalocyanines, methods for their preparation and to certain uses thereof.

There are various criteria which have to be met if a compound is to be successful as a photosensitizer for use in photodynamic therapy. Some of these criteria may include the following:

High quantum yield of reactive species.

Relatively non-toxic to the subject.

Absorb electromagnetic radiation preferentially in the red or near infra-red region of the spectrum.

Selectively attach to tumour.

A compound which is tested for PDT applications may exhibit some but not all of these characteristics. For example a compound might be very efficient at generating reactive species such as singlet oxygen (or other cytotoxic species e.g. free radicals) but may not attach itself selectively if at all to tumours.

It is also advantageous if the photosensitizer absorbs in the red region of the electromagnetic region of the spectrum. Red light shows greater tissue penetration than light of shorter wavelengths. Preferably a photosensitizer absorbs laser light of a suitable wavelength e.g. red or near ir laser radiation.

Other light sources may also be used such as a tungsten halogen lamp.

According to this invention a pharmaceutical composition comprises a compound of formula I in a mixture or in association with a pharmaceutically acceptable carrier or diluent; where formula I is as follows:

formula I

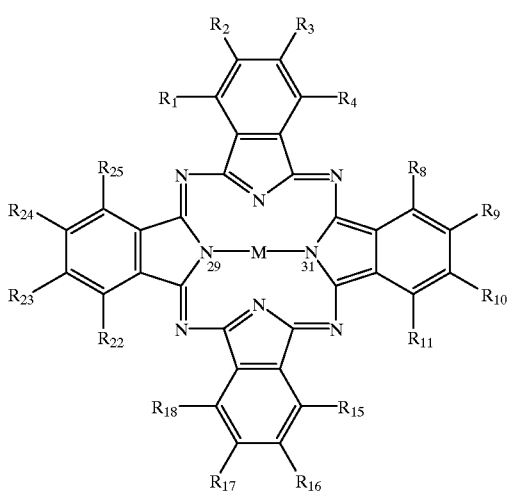

wherein M is a diamagnetic metal atom or a diamagnetic metal compound or silicon or a compound of silicon or is 2H; one H being bonded to each of the two nitrogen atoms depicted as being bonded to M (positions 29 and 31 shown);

$R_1$ and $R_{25}$ are the same or different and are independently selected from $C_1$–$C_{20}$ alkyl, $C_2$–$C_{20}$ alkenyl, X—O—Y,

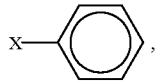

$X^2COOX^1$, $X^2CONR^1R^{11}$ and H;

wherein X and $X^2$ are independently selected from a chemical bond, —$(CH_2)_n$— where n is an integer from 1 to 20 and —$(CH_2)_aCH$=$CH(CH_2)_b$, were a and b are independently selected from integers 0–20 and a+b totals from 0 to 20;

$X^1$ is independently selected from $C_{1-20}$ alkyl, $C_{2-20}$ alkenyl and H;

$R^1$ and $R^{11}$ are independently selected from H; $C_{1-20}$ alkyl, $C_{2-20}$ alkenyl, —$(CH_2)_n$—;

Y is independently selected from $C_{1-20}$ alkyl, $C_{2-20}$ alkenyl and H;

provided that not all $R_1$–$R_{25}$ are simultaneously H.

According to a second aspect of this invention there is provided use of a compound of formula I for the preparation of a medicament for photodynamic therapy.

Preferred compounds for use in the above applications are those of formula I wherein;

$R_{1,4,8,11,15,18,22,25}$ are all alkyl and the remaining R groups are all H, or $R_{1,4,8,11,15,18,22,25}$ are all OH and the remaining R groups are all H, or $R_{1,4,8,11,15,18,22,25}$ are all alkoxy and the remaining R groups are all H, or $R_{1,4,8,11,22,25}$=alkyl and $R_{15,18}$=$X^2COO$-alkyl or $X^2CONR^1R^{11}$ or $X^2COOH$ or

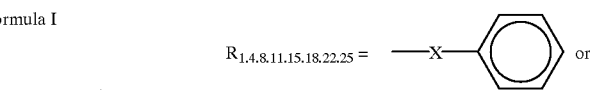

$R_{1,4,8,11,15,18,22,25}$=$X_2CONR^1R^{11}$ or
$R_{1,4,8,11,15,18,22,25}$=alkenyl
wherein $X^2$, $R^1$, $R^{11}$, X and M are as defined above.

Preferably $X^2$ has more than one carbon atom. Particularly preferred alkyl groups for formula I above are those which are n-alkyl containing 4–14 carbon atoms, even more particularly those containing 8–12 carbon atoms. The Pcs of formula I may be metal free (M=2H) or preferably M may be a diamagnetic metal atom. The metal atom may be present as the metal with, for example, an oxidation state of +2 or it may be present with other ligands (or anions) attached to it. These ligands (or anions) may serve the purpose of altering the hydrophobicity of the molecule as a whole. Examples of suitable anions include halides, for example chloride and bromide, other anions include oxides or hydroxides. Examples of suitable metals include Ni, Pb, V, Pd, Co, Nb, Al, Sn, Zn, Cu, Mg, Ca, In, Ga, Fe and Ge. Preferably the metal is zinc.

The synthesis of examples of these materials is described in UK Patent GB 2 229 190 B, U.S. patent application Ser. No. 07/380,437.

The compounds described by the present invention are induced to act as photosensitizers by incident electromagnetic radiation of a suitable wavelength. This includes all suitable wavelengths of the electromagnetic spectrum. Preferably the electromagnetic radiation is somewhere in the range ultra-violet to infra-red, even more preferably it is in the range visible red to infra-red.

Enhanced positioning of the compounds of formula I in relation to treating tumours may be achieved. For example the compounds of formula I may be combined with other chemical moieties. A particular compound from those described by Formula I could be combined, for example by chemical attachment, with an antibody tailored to attach itself to the tumour site. Antibodies are prepared from cultured samples of the tumour. Examples include P.L.A.P. (Placental Alkaline Phosphatase), H.M.F.G. (Human Milk Fat Globulin), C.E.A. (Carcino Embryonic Antibody), H.C.G. (Human Chorionic Gonadotrophin).

Further possible uses of Pcs (as photosensitizers) of formula I are for the following:

Anti-virals in blood-banks.

Insecticides.

The present invention illustrates that these compounds are active in in vitro and in vivo tests.

The present invention provides a pharmaceutical composition comprising a compound of formula I in a mixture or in association with a pharmaceutically acceptable carrier or diluent. The invention also includes a method of treatment of a mammal having a tumour susceptible to photodynamic treatment, wherein the mammal is administered an effective dose of a compound of formula I or a pharmaceutically acceptable salt form thereof and the tumour is subjected to suitable electromagnetic radiation.

The pharmaceutical compositions may be formulated according to well-known principles and may desirably be in the form of unit dosages determined in accordance with conventional pharmacological methods. The unit dosage forms may provide a daily dosage of active compound in a single dose or in a number of smaller doses. Dosage ranges may be established using conventional pharmacological methods and are expected to lie in the range 1 to 60 mg/kg of body weight. Other active compounds may be used in the compositions or administered separately, or supplemental therapy may be included in a course of treatment for a patient. The pharmaceutical compositions may desirably be in the form of solutions or suspensions for injection or in forms for topical application including application in for example the oral cavity. Application in other cavities is also possible. Suitable carriers and diluents are well known in the art and the compositions may include excipients and other components to provide easier or more effective administration.

Following administration to the patient, photodynamic therapy may be carried out in a conventional manner, using light sources and delivery systems that are known in the art, for example see *Phys. Med. biol.* (1986), 31, 4, 327–360.

The invention will now be described by way of example only with reference to the following drawings.

EXAMPLE 1

Figure 1:
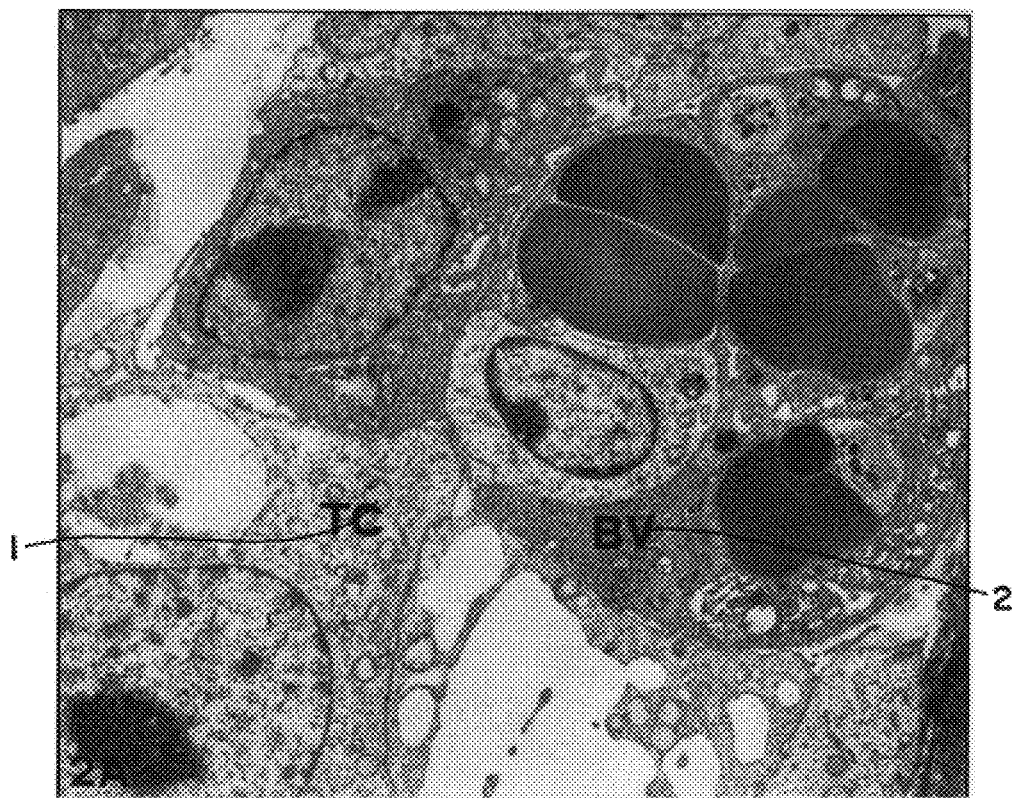
FIG. 1 illustrates a typical micrograph obtained from a tumour specimen isolated at 6 hours after PDT. Magnification 5000× (upper diagram) and 6000×.
Figure 1:
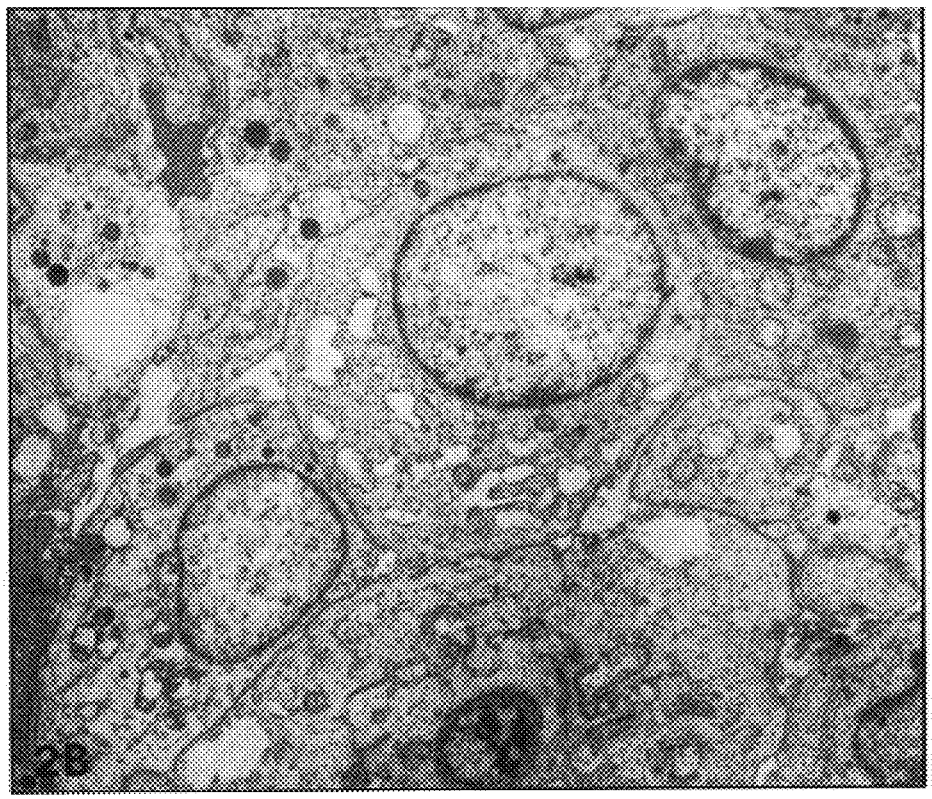

The following compound (abbreviation ZnODPc) was prepared:

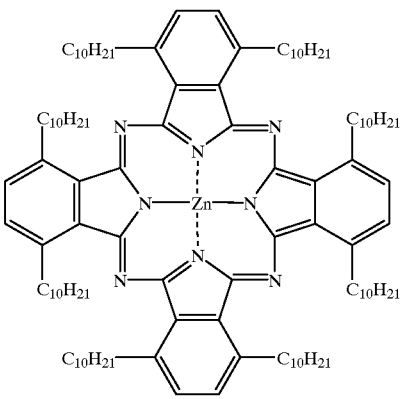

Synthesis of ZnODPc

Metal free 1,4,8,11,15,18,22,25-octakis-decylphthalocyanine (see McKeown et al *J. Chem. Soc. Perkin Trans.* 1, 1169–1177, 1990.) 1.3 g, 0.8 mmol was dissolved in dry pentan-1-ol (25 ml) under reflux. Zinc (II) acetate (500 mg, 2.7 mmol) was added and reflux continued for 45 minutes. The solvent was removed under reduced pressure and the residue purified using column chromatography over silica gel Merck 7734 eluent petroleum ether bp 40–60° C.:toluene (4:1). Recrystalisation from tetrahydrofuran-methanol to afford 1,4,8,11,15,18,22,25-octakis-decylphthalocyaninato-zinc (ZnODPc) as fine blue needles (1.24 g, 91%) m.p. 233.8° C. Elemental Analysis, found: C, 79.18; H, 10.51; N, 6.56%; $C_{112}H_{176}N_8Zn$ requires C, 79.13; H, 10.43; N, 6.59%.

A number of other example compounds (2–7 and 11–12) were synthesised in a similar manner to ZnODPc wherein the length of alkyl chain was varied. Example compounds 2–7 and 11–12 are described by the following general formula II:

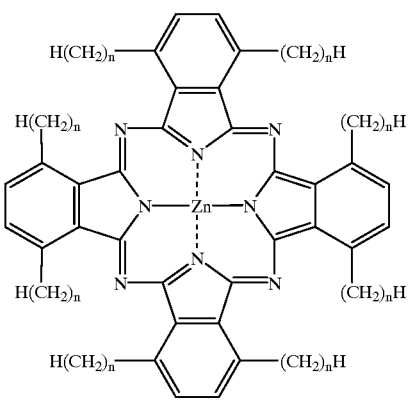

Example 1: n=10, ZnODPc.
Example 2: n=1.
Example 3: n=2.
Example 4: n=4.
Example 5: n=5.
Example 6: n=6.
Example 7: n=8.
Example 11: n=7.
Example 12: n=9.

Other examples of compounds tested include the following:

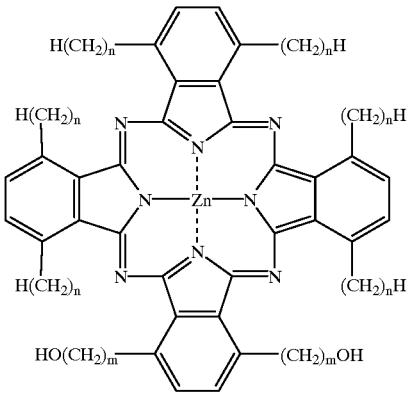

Example 8: m=6, n=9.
Example 9: m=9, n=10.

Compounds 8 and 9 were prepared by reacting together two different phthalonitrile precursors to form the metal-free phthalocyanine and then incorporating zinc. The following describes the synthesis of compound 9.

1,4-Bis (9-Hydroxynonyl)-8,11,15,18,22,25-Hexadecylphthalocyanine 3,6-Bis[9-(tetrahydropyran-2-yloxy)nonyl]phthalonitrile and 3,6-didecyl-phthalonitrile were prepared from furan and thiophene respectively by adaptation of the routes outlined by Chambrier, Cook, Cracknell and M$^c$Murdo in J. Mater. Chem. 1993, 3 (8), 841.

3,6-Bis[9-(tetrahydropyran-2-yloxy)nonyl]phthalonitrile (7 g, 17 mmol) and 3,6-didecyl-phthalonitrile (1.21 g, 2 mmol) were heated to reflux in dry pentan-1-ol (25 ml) and lithium metal (500 mg, 70 mmol) added. After 1 h the mixture was allowed to cool to room temperature. Acetic acid (50 ml) was added and stirring continued for 30 min. The solvents were removed under reduced pressure and the residue triturated with methanol to remove unreacted starting material and lithium salts. The residue was taken up in tetrahydrofuran and filtered to remove the water soluble salts and the solvent removed under reduce pressure. The resultant dark green oil was chromatographed over silica (eluent petroleum ether b.p. 40–60° C.) to afford as the first fraction 1,4,8,11,15,18,22,25-octadecylphthalocyanine which was recrystallised from tetrahydrofuran/acetone to give bright green needles (2 g, 29%) m.p. 77.5° C. (K-D), 133° C. (D-I). $\delta_H$ (400 MHz; solvent $CDCl_3$) 0.0 (2H, s), 0.9 (24H, t), 1.05–2.48 (128H, m), 4.43 (16H, t), 7.78 (8H, s). (Elemental Analysis, found: C, 82.23; H, 11.14; N 6.66; $C_{112}H_{178}N_8$ requires: C, 82.19; H, 10.96; N, 6.85%). The column was eluted with a petrol/dichloromethane mixture 50:50 to remove any remaining octadecyl-phthalocyanine and then a second fraction eluted with petroleum ether b.p. 40–60° C./tetrahydrofurn 9:1 was collected and re-chromatographed four times over silica gel eluent cyclohexane/tetrahydrofuran 9:1 to afford 1,4-bis(9-hydroxynonyl)-8,11,15,18,22,25-hexadecylphthalocyanine which was recrystallised from tetrahydrofuran/methanol to yield dark green cubes {(500 mg, 15%) based on 3,6-bis[9-(tetrahydropyran-2-yloxy)nonyl]phthalonitrile} m.p. 103° C. (K-D), 125° C. (D-I). $\delta_H$ (270 MHz, solvent $d_6$ benzene) −0.15 (2H, s), 0.90 (18H, t), 1.1 (78H, m), 1.42 (16H, m), 1.75 (16H, m), 2.30 (16H, m), 3.25 (4H, t), 4.70 (16H, t), 7.9 (8H, s). (Elemental analysis, found: C, 80.43; H, 10.64; N, 6.94; $C_{110}H_{174}N_8O_2$ requires: C, 80.53; H, 10.69; N, 6.82%).

1,4-Bis (9-Hydroxynonyl)-8,11,15,18,22,25-Hexadecylphthalocyaninato-Zinc 1,4-Bis (9-hydroxynonyl)-8,11,15,18,22,25-hexadecylphthalocyanine (200 mg) was converted into 1,4-Bis(9-hydroxynonyl)-8,11,15,18,22,25-hexadecylphthalocyaninato-zinc (80 mg) following the procedure described for ZnODPc, (80%) m.p. 125.1° C. (Elemental Analysis, found: C, 77.51; H, 10.15; N, 6.32; $C_{110}H_{172}N_8O_2Zn$ requires: C, 77.54; H, 10.17; N 6.58%).

Compound 8 was prepared by the same procedure.

TABLE A

Characterisation of 1,4,8,11,15,18,22,25-Octasubstituted Zinc Phthalocyanines

| Comp. | Yield[a] | M.p.[b] ° C. | Found (Requires) C | H | N | Q Band[c] |
|---|---|---|---|---|---|---|
| 1 | 91 | 89.6 (K-D) 225.1 (D-I) | 79.30 (79.13) | 10.77 (10.43) | 6.61 (6.59) | 705(1.82),672(sh), 635(0.34) |
| 2 | 73 | >300 | 69.38 (69.61) | 4.65 (4.67) | 15.90 (16.24) | 703,669.632 |
| 3 | 70 | >300 | 71.74 (71.86) | 5.73 (6..03) | 13.81 (13.97) | 703,669,632 |
| 4 | 74 | 296.1 | 75.08 (74.87) | 7.99 (7.85) | 10.75 (10.91) | 705,669(sh),634 |
| 5 | 64 | 278.7 (K-D) 291.9 (D-I) | 75.90 (75.93) | 8.74 (8.50) | 9.84 (9.84) | 702,669(sh),633 |
| 6 | 72 | 209.3 (K-D) 285 (D-I) | 76.72 (76.80) | 9.04 (9.02) | 8.83 (8.96) | 705(1.72),671(sh), 634(0.34) |
| 7 | 68 | 104.8 (K-D) 258 (D-I) | 78.02 (78.14) | 9.92 (9.84) | 7.60 (7.59) | 701(1.77),677(sh), 633(0.34) |
| 8 | ca70 | 132.6 (K-D) 161.8 (D-I) | 75.78 (76.65) | 9.77 (9.71) | 6.98 (7.30) | 704,670,635 |
| 9 | 80 | 125.1 | 77.51 (77.54) | 10.15 (10.17) | 6.32 (6.58) | 704,670,634 |
| 11 | 66 | 158.4 (K-D) 271.6 (D-I) | 77.31 (77.52) | 9.69 (9.46) | 8.15 (8.22) | 703,667(sh),633 |
| 12 | 71 | 113.9 (K-D) 242 (D-I) | 78.41 (78.67) | 10.36 (10.16) | 6.93 (7.06) | 703,669(sh),634 |

[a]from the metal free derivatives.
[b]K = crystal state, D = discotic mesophase, I = isotropic liquid.
[c]$\lambda_{max}$ (cyclohexane) nm ($\epsilon \times 10^5$)

Spectroscopic Properties of ZnODPc

Spectroscopic data for ZnODPc in cyclohexane were determined as follows: molar absorption coefficient ($\epsilon$) at the absorption maximum of 703 nm was found to be approximately $2.3 \times 10^5$ $dm^3$ $mol^{-1}$ $cm^{-1}$. The fluorescence emission maximum, excited at 703 nm is at 712 nm.

Tumour Investigation

In this investigation female Balb/c mice 20–22 g bearing a MS-2 fibrosarcoma intramuscularly implanted into the hind right leg were used as an animal model. On the 7th day after transplantation when the tumour diameter was 0.6–0.8 cm and no spontaneous necrosis could be detected, the mice were injected with 1.2 or 2.4 mg/kg ZnODPc incorporated into Cremophor emulsions. The preparation and characterisation of such emulsions has been described by L. Polo et al Cancer Lett. 66: 217–223, 1992. The amount of injected ZnODPc was estimated by diluting a known aliquot of the phthalocyanine-containing emulsion into THF and reading the absorbance at 701 nm (molar absorption coefficient $2.01 \times 10^5$ $dm^3$ $mol^{-1}$ $cm^{-1}$).

Singlet Oxygen Generation

The material ZnODPc generates singlet oxygen with a quantum yield of 0.73±0.06 in toluene/pyridine solution. This can be compared with unsubstituted phthalocyanine containing zinc in ethanolic solution which has a quantum yield of approximately 0.4, see G. Valduga et al, *Photochem. Photobiol.*, vol 48, page 1 1988.

Pharmacokinetic Studies

The tumour-bearing mice were injected with 1.2 mg/kg ZnODPc in the tail vein. At 3 hours and 24 hours after administration, groups of three mice were sacrificed by prolonged exposure to ether vapours, the tumour and selected normal tissues (muscle, skin, liver and kidneys) were excised, washed with phosphate buffered saline (PBS) and assayed for the phthalocyanine content by spectrofluorimetric analysis after chemical extraction, see Reddi et al *Br. J. Cancer* 61: 407–411, 1990; typically a weighted amount of tissue was homogenized in 3 ml of 2% aqueous sodium dodecyl sulphate (SDS); the homegenate was incubated for 1 hour at room temperature under gentle magnetic stirring and 1 ml of the suspension was added with 2 ml of THF, centrifuged at 10 mins at 3000 rpm; the supernatant was collected and its fluorescence intensity was determined in the 670–770 nm interval (excitation at 650 nm). The fluorescence intensity was converted into ZnODPc concentration by interpolation with a calibration plot. Samples of blood were taken from the sacrificed animals, centrifuged to separate the erythrocytes and the serum (50 $\mu$l) thus collected was diluted with 2% aqueous SDS (700 $\mu$l), added with 1.5 ml of THF and centrifuged for 10 mins at 3000 rpm. The ZnODPc concentration in the supernatant was determined by fluorescence spectroscopy as specified above.

Phototherapeutic Studies

The tumour bearing mice were injected with 2.4 mg/kg ZnODPc and after 24 h were irradiated by 600–700 nm light which was isolated from the emission of a quartz-halogen lamp (Teclas, Lugano Switzerland) by optical filtering. The light beam was focussed into a bundle of optical fibres, whose tip was positioned at a 1 cm distance from the tumour surface. The lamp was operated at 230 mW/cm$^2$ for a total delivered light dose of 400 J/cm$^2$.

The tumour response was analyzed by visual observation, as well as by electron microscopy studies on tumour specimens taken at 6 h and 24 h after the end of the PDT. The procedure for the preparation of the samples and ultra structural determinations was performed as described by Milanesi et al. *Br. J. Cancer* 61: 846–850, 1990.

Results

The recoveries of ZnODPc from serum, tumour and selected normal tissues of Balb/c mice are reported in Table 1.

TABLE 1

Recovery ($\mu$g of dye/g of tissue) of ZnODPc i.v.-injected (1.2 mg/kg) to Balb/c mice bearing a Ms-2 fibrosarcoma.

| Tissue | Recovery 3 h | Recovery 24 h |
| --- | --- | --- |
| Tumour | 0.073 ± 0.001 | 0.132 ± 0.022 |
| Muscle | nd | nd |
| Liver | 0.278 ± 0.053 | 0.673 ± 0.140 |
| Kidney | 0.066 ± 0.008 | 0.005 ± 0.002 |
| Skin | nd | 0.008 ± 0.001 |
| Serum* | 0.436 ± 0.324 | 0.042 ± 0.015 | nd = not detected
*pg/ml

Special attention was focussed on the phthalocyanine content in the muscle which is the peritumoural tissue in the animal model exemplified in this study and the skin because of the frequent onset of persistent cutaneous photosensitivity in PDT patients. The determination of ZnODPc accumulation in liver and kidneys can provide useful information on the modality of its elimination from the organism. Analyses were carried out at 3 h intervals after photosensitizer injection and at 24 h which is generally considered to be the usual time interval for PDT treatment.

Figure 2:
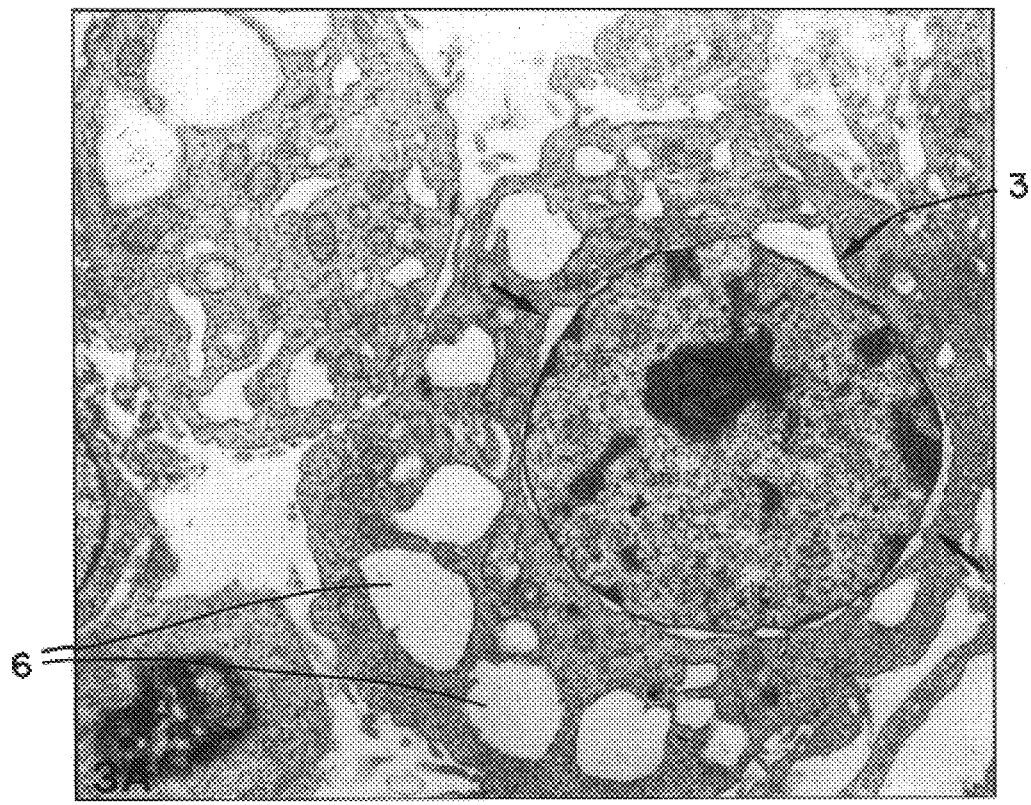
FIG. 2 illustrates a typical micrograph obtained from a tumour specimen isolated at 24 hours after PDT. Magnification 7,500× (upper diagram) and 4000×.
Figure 2:
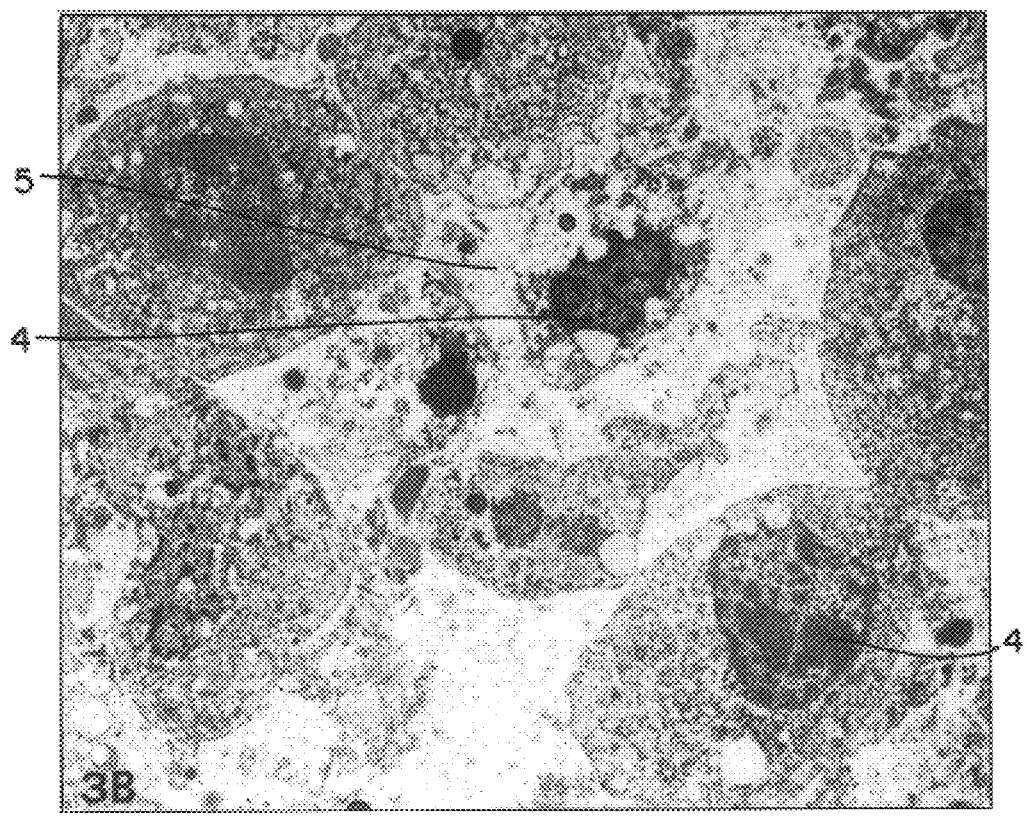

All subsequent radiation experiments were performed at 24 h post-injection since the ZnODPc concentration in the tumour appears to be still increasing at this time. In all cases photosensitized mice showed a significant delay in tumour growth as compared with untreated tumour-bearing mice. As shown in FIG. 1 at 6 h after irradiation one can observe extensive damage of tumour cells 1 especially at the cytoplasmic level, while blood vessels 2 appear to be less heavily damaged. The tissular damage is remarkably more extensive at 24 h after irradiation (see FIG. 2) involving also the perinuclear membrane 3 of malignant cells while several nuclei are pyknotic 4; some nuclear areas appear to be optically empty 5. At the same time endocytoplasmic vacuolisation 6 is frequently observed with some completely necrotic cells and loss of the organised tissue structure. Overall the tumour appears to be deeply haemorrhagic.

Triplet state studies were carried out using laser flash photolysis. Samples were prepared in a 1% pyridine in toluene solution; by preparing such a solution then it is believed that aggregation of the phthalocyanine cores is avoided. The solution was prepared so that an optical density of 0.2–0.3 at the excitation wavelength was obtained. Samples were irradiated by an excimer pumped dye laser at 355 nm and the transients monitored with the use of a quartz halogen lamp. Triplet quantum yields were calculated using ZnTPP and ZnPc as standards. The results are presented in Table 2. The triplet quantum yield is the quantum yield of conversion from the excited singlet state to the triplet state.

TABLE 2

| Compound (example no.) | Triplet Lifetime/$\mu$s | Triplet Quantum Yield |
| --- | --- | --- |
| 1 | 50 | 0.67 |
| 2 | 150 | 0.62 |
| 3 | 49 | 0.81 |
| 4 | 50 | 0.67 |
| 5 | 49 | 0.75 |
| 6 | 51 | 0.71 |
| 7 | 50 | 0.77 |
| 8 | 50 | 0.62 |
| 9 | 50 | 0.70 |
| 10 | 302 | 0.45 |

Compound example 10 is unsubstituted zinc phthalocyanine (ZnPc); this is included in the Table for means of comparison.

The data in Table 2 are means of no less than four independent runs, except for compounds 8 and 9 which were run once.

The generation of singlet oxygen by the phthalocyanines was also studied. The method of detection of the singlet oxygen involved measuring the intensity of luminescence at 1270 nm, corresponding to the forbidden transition from the excited singlet back down to the ground state, with a liquid nitrogen cooled germanium detector. Aerated samples were irradiated with the same system as described for the triplet state studies. Standards used were ZnTPP, ZnPc and anthracene.

TABLE 3

| Compound (example no.) | Singlet Oxygen Quantum Yield |
|---|---|
| 1 | 0.73 |
| 2 | 0.64 |
| 3 | 0.58 |
| 4 | 0.80 |
| 5 | 0.64 |
| 6 | 0.66 |
| 7 | 0.75 |
| 8 | 0.65 |
| 9 | 0.80 |
| 10 | 0.50 |

The data in Table 3 are means of no less than four independent runs, except for compounds 8 and 9 were run once.

The properties of the decomposition products arising from irradiation of the phthalocyanines were investigated. It is believed that substituted phthalimides are the major product of the decomposition. Results obtained from the irradiation of a solution of ZnODPc (example compound 1) in 1% pyridine in toluene indicate that the singlet oxygen quantum yield of the decomposition mixture is not more than 0.05.

These results clearly demonstrate that the present invention provides promising PDT agents owing to highly selective localisation in the tumour tissue. Considering, for example the ZnODPc example, comparatively low ZnODPc concentrations are found in the liver even though clearance of the photosensitizer from the organism must occur by the bile-gut pathway, since negligible amounts are accumulated in kidneys. Moreover essentially no phthalocyanine is present in cutaneous districts thus minimising the side-effects due to skin photosensitization. No detectable amount of phthalocyanine was recovered from the peritumoural tissue at the post-injection times investigated, while the amount of ZnODPc accumulated in the fibrosarcoma is sufficient for inducing an efficient tumour damage upon photoexcitation with red light. It is a particular advantage of the present invention that the compounds absorb light in the red region of the spectrum. Under the irradiation conditions described here, malignant cells appear to be the main target of, for example, ZnODPc photosensitization although an appreciable damage of blood capillaries is also observed. In general, PDT agents which are administered in combination with lipid-type delivery systems induce tumour necrosis via early injury to neoplastic cells while vascular damage is observed only at later times after irradiation possibly as a secondary consequence of cellular damage, for example leakage of intracellular material into the bloodstream. It has been illustrated by the present invention that both cellular and vascular compartments of the neoplastic tissue are clearly affected in the initial stages of the photodamaging process.

The mechanism of tumour photosensitization by the photosensitizer is in some cases, e.g. ZnODPc, also characterised by the appearance of extensive damage of cell nuclei which becomes pyknotic and optically empty. This is different from what is observed for other hydrophobic phthalocyanines, where the sensitized damage is usually confined to cell membranes even after drastic irradiation protocols, for example see Milanei et al *Br. J. Cancer:* 846–850, 1990.

The parallel damage of both malignant cells and capillaries could enhance the response of the tumour tissue to PDT treatment.

In another embodiment of the invention, M in formula I may be a non-metal other than silicon or compounds of silicon.

What is claimed is:

1. A method of treating susceptible tumors comprising sensitizing the tumor or tumors to incident electromagnetic radiation by administering to a subject in need of same a tumor sensitizing effective amount of a compound of the formula:

formula I

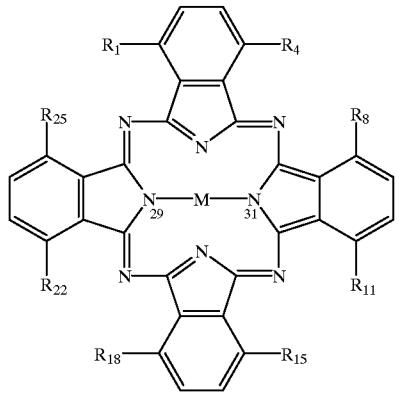

wherein M is a diamagnetic metal ion or a diamagnetic metal compound or silicon or a compound of silicon or is 2H; one H being bonded to each of the two nitrogen atoms depicted as being bonded to M at positions 29 and 31;

$R_1$ to $R_{25}$ are the same or different and are independently selected from $C_1$–$C_{20}$, alkyl, $C_2$–$C_{20}$ alkenyl, X—O—Y,

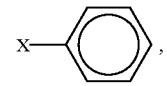

$X^2COOX^1$, $x^2COONR^1R^{11}$ and H;

wherein X and $X^2$ are independently selected from a chemical bond, —$(CH_2)_n$— where n is an integer from 1 to 20 and —$(CH_2)_a CH= CH(CH_2)_b$ where a and b are independently selected from integers 0–20 and a+b totals from 0 to 20;

$X^1$ is independently selected from $C_{1-20}$ alkyl, $C_{2-20}$ alkenyl and H $R^1$ and $R^{11}$ are independently selected from H, $C_{1-20}$ alkyl, $C_{2-20}$ alkenyl; and Y is independently selected from $C_{1-20}$ alkyl, $C_{2-20}$ alkenyl and H;

provided that not all $R_1$–$R_{25}$ are simultaneously H; and provided that not all $R_1$–$R_{25}$ are simultaneously n-alkoxy, and thereafter exposing the tumor or tumors so treated to incident electromagnetic radiation absorbed by the compound.

2. The method of claim 1 wherein $R_{1,4,8,11,15,18,22,25}$ are all alkyl.

3. The method of claim 1 wherein $R_{1,4,8,11,15,18,22,25}$ are all n-alkyl containing 4–14 carbon atoms.

4. The method of claim 1 wherein $R_{1,4,8,11,15,18,22,25}$ are all n-alkyl containing 8–12 carbon atoms.

5. The method of claim 1 wherein $R_{1,4,8,11,22,25}$ are al alkyl and both $R_{15,18}$ are —$(CH_2)_n$—$COOR^1$ where n is 1 to 10 and $R^1$ is an alkyl group containing 1 to 10 carbon atoms.

6. The method of claim 5 wherein n is 3 and $R^1$ is n-alkyl.

7. The method of claim 1 wherein $R_{1,4,8,11,15,18,22,25}$ are all —$CH_2$O-alkyl groups, where the alkyl groups contain 3–12 carbon atoms.

8. The method of claim 7 wherein $R_{1,4,8,11,15,18,22,25}$ are al n-alkyl.

9. The method of claim 1 wherein M is a diamagnetic metal atom or is 2H.

10. The method of claim 1 characterised in that M is a diamagnetic metal.

11. A method according to claim 10 characterised in that M is zinc.

12. The method of claim 1 characterised in that M is 2H.

13. The method of claim 1 characterised in that M is a diamagnetic metal compound.

14. The method of claim 13 characterised in that the diamagnetic metal compound is chosen from halometal, oxymetal or hydroxymetal.

15. The method of claim 1 wherein:

$R_{1,4,8,11,15,18,22,25}$ are all alkyl and the remaining R groups are all H, or $R_{1,4,8,11,15,18,22,25}$ are all OH and the remaining R groups ae all H, or $R_{1,4,8,11,22,25}$ are alkyl and $R_{15,18}$=$X^2$COO-alkyl or $X^2CONR^1R^{11}$ or $X^2$COOH, or $R_{1,4,8,11,15,18,22,15}$ are

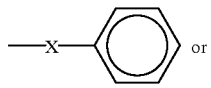 or $R_{1,4,8,11,15,18,22,25}$ are $X^2CONR^1R^{11}$ or $R_{1,4,7,8,11,15,18,22,25}$ are alkenyl wherein $X^2$, $R^1$, $R^{11}$, X and M are as defined in claim 1.

16. The method of claim 15 wherein $R_{1,4,8,11,15,18,22,25}$ are all alkenyl groups of formula —$(CH_2)_n$—CH=CH—Z where n is 0 to 10 and Z is H or alkyl, the whole alkenyl group containing 2 to 20 carbon atoms.

17. The method of claim 16 wherein $R_{1,4,8,11,15,18,22,25}$ are all —$(CH_2)_n$CH=$CH_2$.

18. The method of claim 15 wherein $R_{1,4,8,11,22,25}$ are all alkyl and $R_{15,18}$ is —$X^2$COO-alkyl, $X^2$COOH or $X^2CONR^1R^{11}$.

19. The method of claim 13 wherein $R_{1,4,8,11,22,25}$ are all $C_{8-10}$ alkyl and $R_{15,18}$ is —$X^2$COOH with $X^2$ being a chemical bond or —$(CH_2)_a$— where a is 1 to 6.

20. A method of treating susceptible tumors comprising sensitizing the tumor or tumors to incident electromagnetic radiation by administering to a subject in need of same a tumor sensitizing effective amount of a compound of the formula:

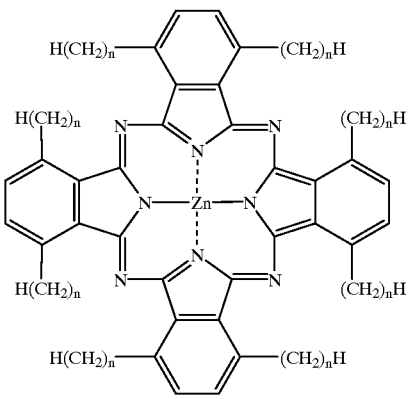

formula II wherein n is from 1–20 and thereafter selectively irradiating the tumor with electromagnetic radiation.

* * * * *